(12) United States Patent
Fabien et al.

(10) Patent No.: US 12,186,480 B2
(45) Date of Patent: Jan. 7, 2025

(54) DEVICE FOR INHALATION SYNCHRONIZED DISPENSING OF A FLUID PRODUCT

(71) Applicant: APTAR FRANCE SAS, Le Neubourg (FR)

(72) Inventors: David Fabien, Saint Renan (FR); Matthieu Cavatorta, Autouillet (FR); Jeremy Tournois, Saint Etienne du Rouvray (FR); Matthieu Walter, Villepreux (FR)

(73) Assignee: APTAR FRANCE SAS, Le Neubourg (FR)

( * ) Notice: Subject to any disclaimer, the term of this patent is extended or adjusted under 35 U.S.C. 154(b) by 688 days.

(21) Appl. No.: 17/427,682

(22) PCT Filed: Feb. 3, 2020

(86) PCT No.: PCT/FR2020/050170
§ 371 (c)(1),
(2) Date: Aug. 2, 2021

(87) PCT Pub. No.: WO2020/161420
PCT Pub. Date: Aug. 13, 2020

(65) Prior Publication Data
US 2022/0126037 A1 Apr. 28, 2022

(30) Foreign Application Priority Data
Feb. 4, 2019 (FR) ...................................... 1901076

(51) Int. Cl.
*A61M 15/00* (2006.01)
(52) U.S. Cl.
CPC ...... *A61M 15/0095* (2014.02); *A61M 15/002* (2014.02); *A61M 15/0025* (2014.02);
(Continued)

(58) Field of Classification Search
CPC ............ A61M 15/0095; A61M 15/002; A61M 15/0025; A61M 15/008; A61M 15/009;
(Continued)

(56) References Cited

U.S. PATENT DOCUMENTS

| 5,060,643 A | 10/1991 | Rich et al. | |
|---|---|---|---|
| 8,807,131 B1 * | 8/2014 | Tunnell | A61M 15/0021 128/200.14 |

(Continued)

FOREIGN PATENT DOCUMENTS

| GB | 2398065 A | * | 8/2004 | .......... A61M 15/008 |
|---|---|---|---|---|
| WO | WO-2006119766 A1 | * | 11/2006 | ........ A61M 15/0071 |

(Continued)

OTHER PUBLICATIONS

International Preliminary Report on Patentability (with translation of the Written Opinion) dated Aug. 10, 2021, issued by the International Bureau in application No. PCT/FR2020/050170.
(Continued)

*Primary Examiner* — Michael R Reid
*Assistant Examiner* — Tyler A Raubenstraw
(74) *Attorney, Agent, or Firm* — Sughrue Mion, PLLC

(57) ABSTRACT

The invention relates to a device comprising a body (10), a reservoir (100) mounted in an axially slidable manner relative to said body (10), a metering valve (200) assembled on said reservoir (100), said device comprising: —a blocking element (500), —a triggering element (600), —a triggering system controlled by inhalation (60) cooperating with said triggering element (600), and —an actuating member (800) cooperating with said blocking element (500), said device comprising an automatic valve release system which automatically returns said valve (210) of said valve (200) to its rest position after actuation of the valve regardless of the position of said actuating member (800).

21 Claims, 7 Drawing Sheets

Figure 1:
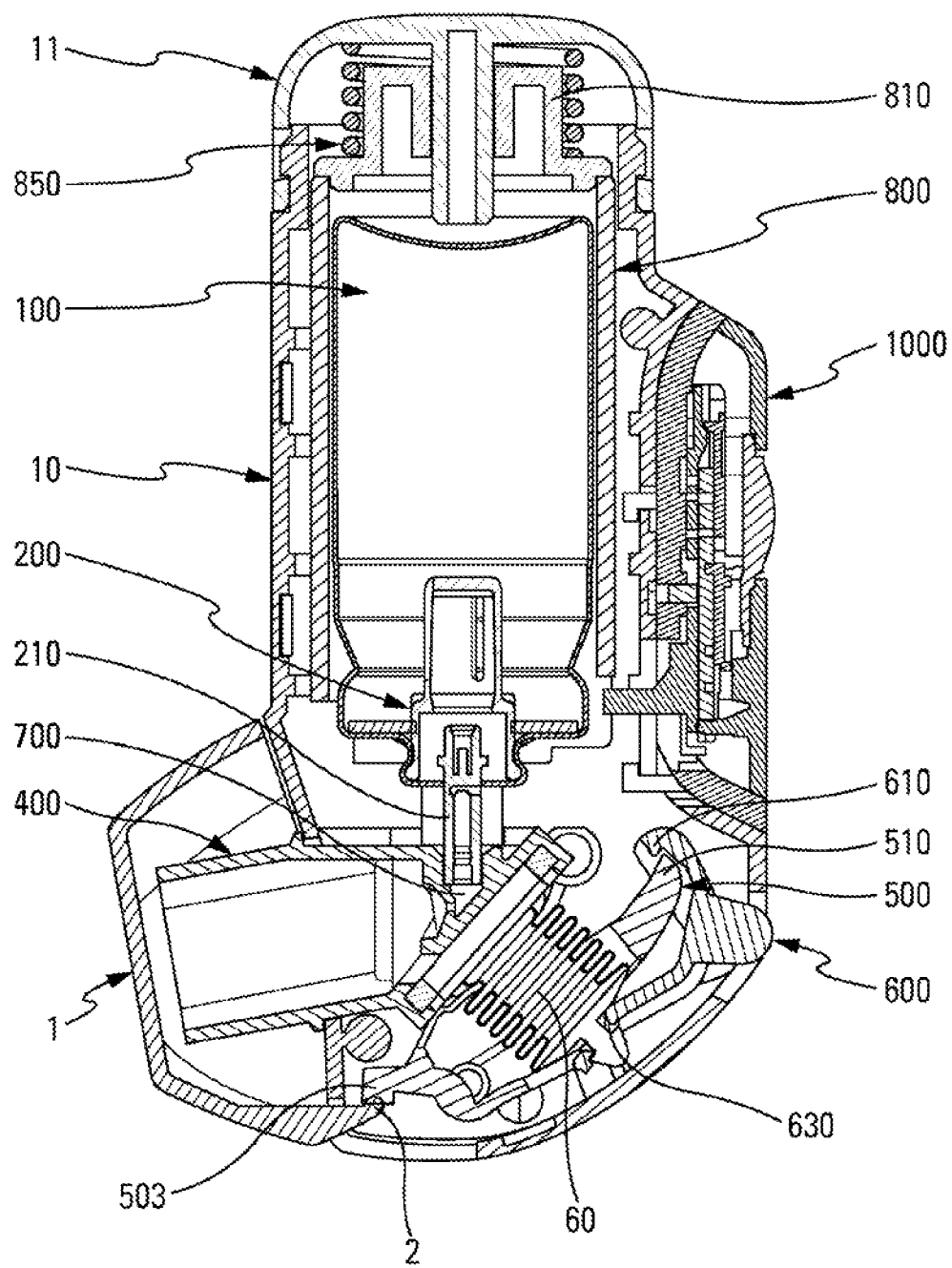

(52) U.S. Cl.
CPC ........ *A61M 15/008* (2014.02); *A61M 15/009* (2013.01); *A61M 2205/3327* (2013.01); *A61M 2205/581* (2013.01); *A61M 2205/583* (2013.01)

(58) Field of Classification Search
CPC .... A61M 2205/3327; A61M 2205/581; A61M 2205/583
See application file for complete search history.

(56) References Cited

U.S. PATENT DOCUMENTS

| | | | | |
|---|---|---|---|---|
| 2004/0139965 A1* | 7/2004 | Greenleaf | ............... | B65D 83/54 128/205.24 |
| 2007/0084467 A1* | 4/2007 | Scarrott | ............ | A61M 15/0065 128/205.23 |
| 2009/0229604 A1* | 9/2009 | Pearson | ............ | A61M 15/0081 128/202.22 |
| 2011/0126836 A1* | 6/2011 | Winter | ................ | A61M 16/205 128/205.12 |
| 2013/0042865 A1* | 2/2013 | Monsees | ................ | G05B 11/36 128/203.27 |
| 2013/0061850 A1* | 3/2013 | Bowman | ............ | A61M 15/007 128/200.14 |
| 2014/0216444 A1* | 8/2014 | Shtram | ............... | A61M 15/008 128/200.23 |
| 2015/0122249 A1* | 5/2015 | Bowman | ............ | A61M 15/007 128/200.23 |
| 2016/0106935 A1* | 4/2016 | Sezan | ............... | A61M 15/0066 128/203.14 |
| 2016/0144141 A1* | 5/2016 | Biswas | ............... | A61M 15/009 128/200.23 |
| 2016/0144142 A1* | 5/2016 | Baker | ................. | A61M 15/008 128/200.23 |
| 2017/0304563 A1* | 10/2017 | Adelson | ............. | A61M 15/003 |
| 2018/0140786 A1* | 5/2018 | Calderon Oliveras | ...................... | A61M 15/0091 |
| 2018/0228989 A1* | 8/2018 | Buck | ................. | A61M 15/0095 |
| 2019/0015609 A1* | 1/2019 | Buck | ................. | A61M 15/0066 |
| 2019/0134322 A1* | 5/2019 | Fabien | ............... | A61M 15/009 |
| 2019/0351160 A1* | 11/2019 | Stuart | ............... | A61M 15/0091 |

FOREIGN PATENT DOCUMENTS

| | | | | |
|---|---|---|---|---|
| WO | 2017/112451 A1 | 6/2017 | | |
| WO | 2017/178764 A1 | 10/2017 | | |
| WO | WO-2017176704 A1 * | 10/2017 | .......... | A61M 15/002 |
| WO | 2018/048795 A1 | 3/2018 | | |

OTHER PUBLICATIONS

International Search Report of PCT/FR2020/050170 dated May 20, 2020 [PCT/ISA/210].

* cited by examiner

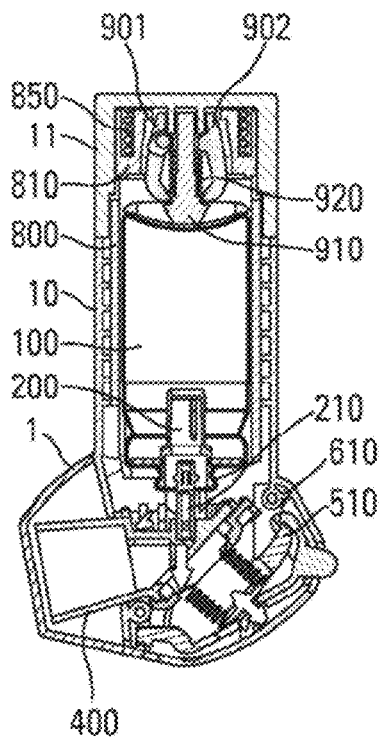
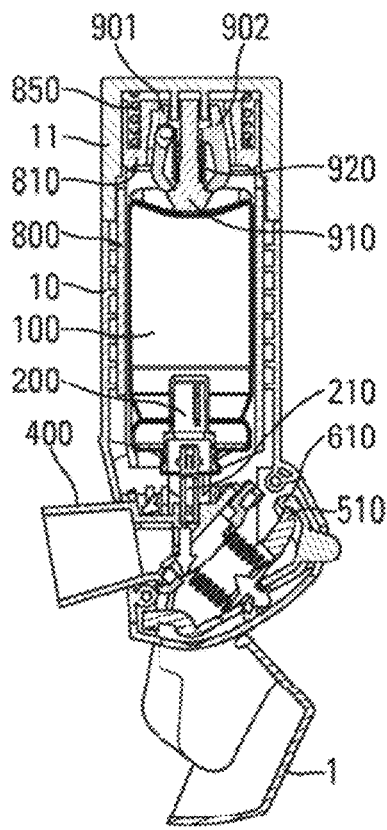
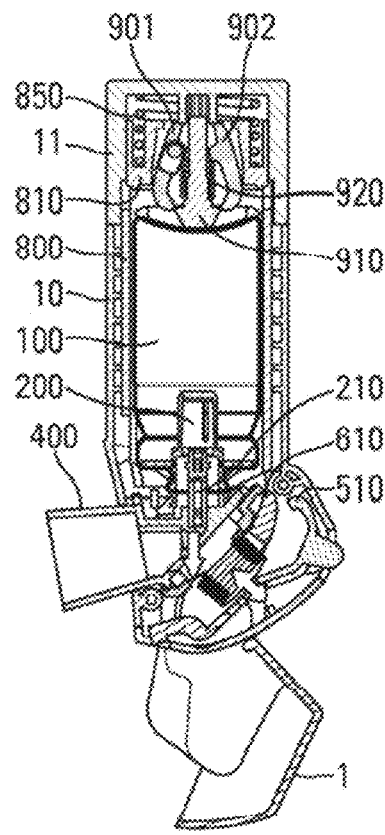
Fig. 13  Fig. 14  Fig. 15
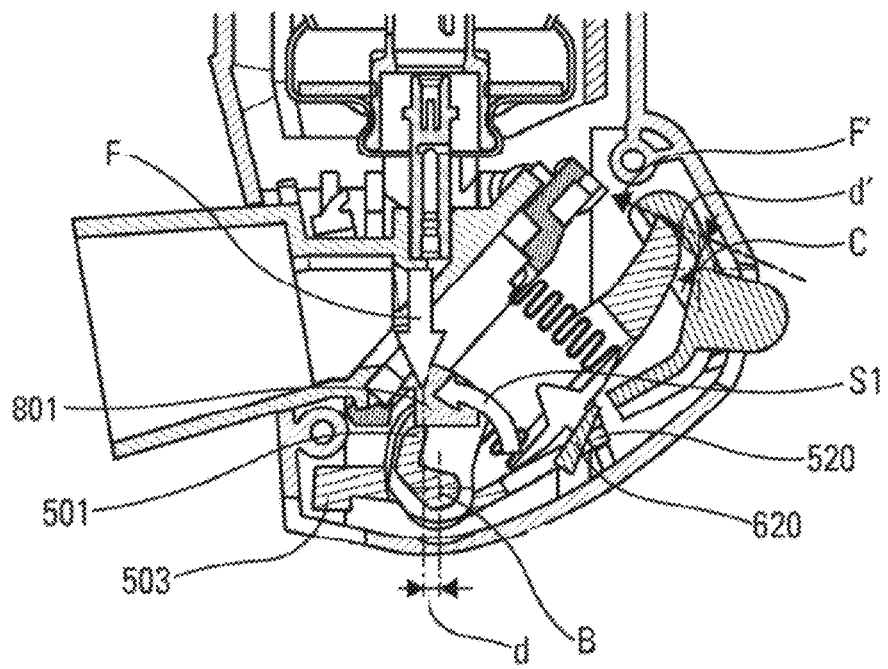
Fig. 16

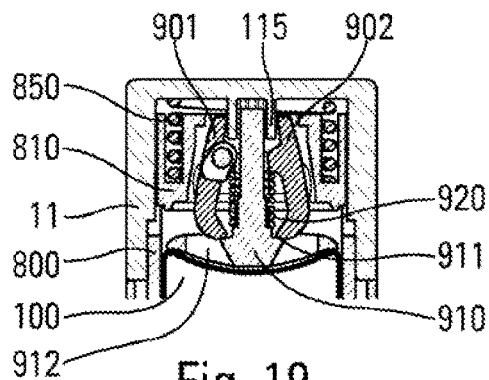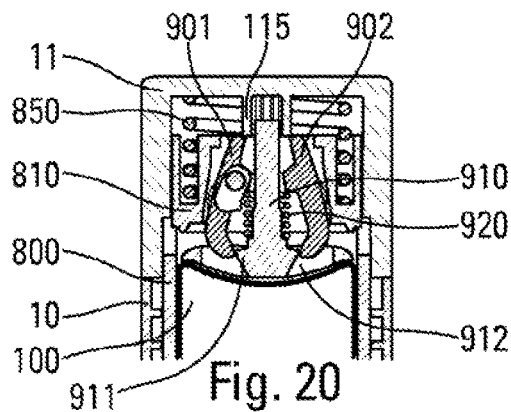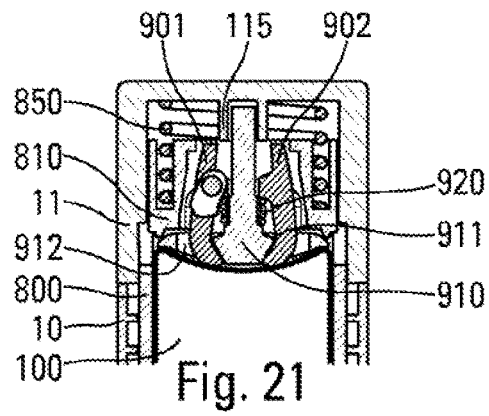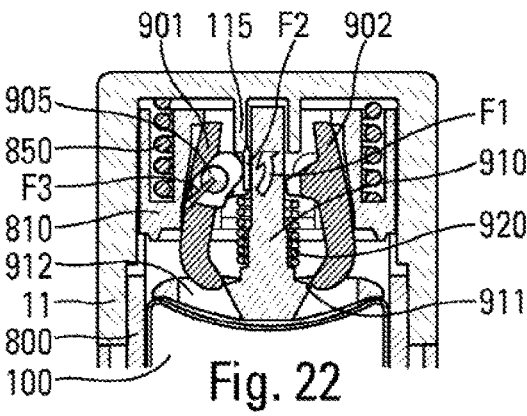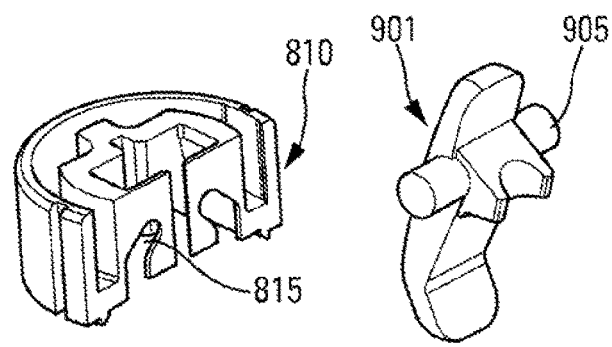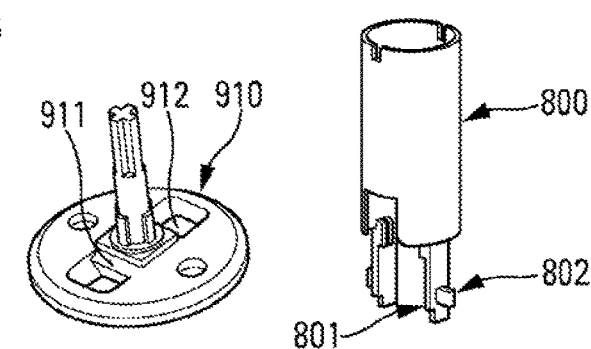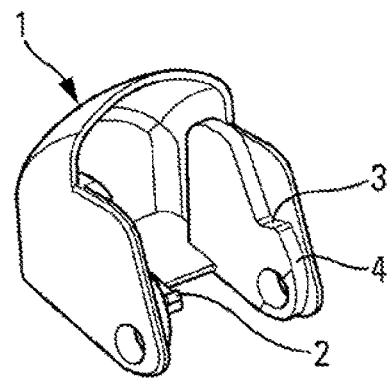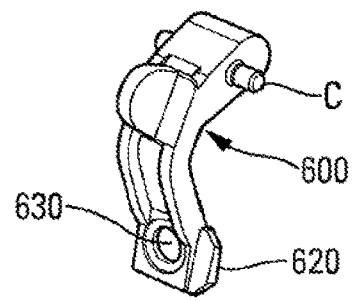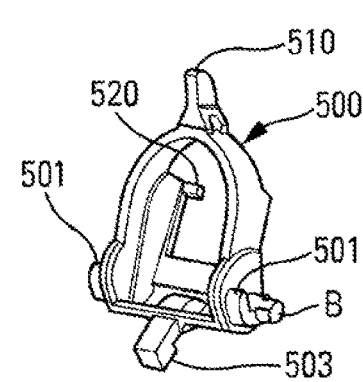

DEVICE FOR INHALATION SYNCHRONIZED DISPENSING OF A FLUID PRODUCT

CROSS REFERENCE TO RELATED APPLICATIONS

This application is a National Stage of International Application No. PCT/FR2020/050170 filed on Feb. 3, 2020, claiming priority based on French Patent Application No. 1901076 filed on Feb. 4, 2019.

The present invention relates to a fluid product dispenser device in which dispensing is synchronized with inhaling, and more particularly it relates to an inhaler device of the aerosol type synchronized with inhaling.

Inhaler actuated devices, commonly referred to as B.A.I. (meaning "Breath Actuated Inhaler"), are well known in the prior art. The main advantage of this type of device is that the dispensing of product is synchronized with the patient inhaling, so as to guarantee that the product is properly dispensed into the airways. Thus, in the field of aerosol devices, i.e. devices wherein the fluid is dispensed by means of a propellant gas, numerous types of breath actuated inhaler device have been proposed. However, those devices present the drawback of comprising a large number of parts, i.e. they are complicated and costly to manufacture and to assemble, which is obviously disadvantageous. It is also difficult to find the right balance between reliable triggering on each inhalation, without the trigger threshold being too high, and a latch that is robust enough to prevent accidental or unwanted actuation. Unfortunately, when the latch releases accidentally, the device is actuated automatically and the dose is dispensed, even when the user does not want it. Another drawback of existing devices is that the valve is generally under stress before the user inhales, sometimes even during the periods of storage between two actuations, with consequently risks of leaks and malfunctions of the valve. Moreover, in existing devices, the valve generally remains in the actuated position after inhalation, until the user returns the device to its rest position, for example by closing the cap. Here too there is a risk of leakage into the valve, with consequently the next dose which may be incomplete and/or a loss of the fluid product contained in the reservoir.

Documents WO 2017/178764, WO 2018/048795, WO 2017/112451, U.S. Pat. No. 5,060,643, WO 2004/028608, U.S. Pat. Nos. 3,456,646, 5,119,806, NZ 562 769, US 2008/156321, WO 2008/070516, WO 2010/003846, and WO 2013/178951 describe prior-art devices.

An object of the present invention is to provide an inhalation-synchronized fluid product dispenser device that does not have the above-mentioned drawbacks.

Another object of the present invention is to provide an inhalation-synchronized fluid product dispenser device that improves operational reliability by guaranteeing effective actuation and dosage precision on each inhalation.

Another object of the present invention is to provide an inhalation-synchronized fluid product dispenser device that minimises the risks of accidental or unwanted actuation.

Another object of the present invention is to provide an inhalation-synchronized fluid product dispenser device that minimises the risks of leakage in the valve, before and/or after inhalation.

Another object of the present invention is to provide an inhalation-synchronized fluid product dispenser device that does not have a trigger threshold that is too high, thereby making it possible for people who are relatively weak, such as the sick or the elderly, to use the device in a safe and reliable manner.

Another object of the present invention is to provide an inhalation-synchronized fluid product dispenser device that is simple and inexpensive to manufacture and to assemble.

Another object of the present invention is to provide an inhalation-synchronized fluid product dispenser device that avoids the risks of the valve malfunctioning as a result of the valve chamber not filling properly after actuation.

The present invention thus provides an inhalation-synchronized fluid product dispenser device comprising a body provided with a mouthpiece, a product reservoir containing a fluid product and a propellant gas being mounted to slide axially relative to said body, a metering valve comprising a valve member being assembled on said reservoir for selectively dispensing the fluid product, said device comprising:
  a blocking element that is movable and/or deformable between a blocking position in which said metering valve cannot be actuated, and an actuation position in which said metering valve, can be actuated,
  a trigger element that is movable and/or deformable between a locking position in which it blocks said blocking element in its blocking position, and a release position wherein it does not block said blocking element,
  an inhalation-controlled trigger system comprising an inhalation-sensitive member that is deformable and/or movable under the effect of inhaling, said inhalation-sensitive member cooperating with said trigger element, such that when said inhalation-sensitive member is deformed and/or moved, it moves and/or deforms said trigger element towards its release position, thus making it possible to move and/or deform said blocking element from its blocking position towards its actuation position, and
  an actuating member that is movable between a rest position and an actuation position under the effect of a spring, said actuating member cooperating with said blocking element, such that in blocking position said blocking element, said blocking element prevents an axial movement of said actuating member, and in actuation position said blocking element, said blocking element makes it possible to move said actuating member axially,
  said device comprising an automatic valve release system, which automatically returns said valve member from said valve towards its rest position after actuation of the valve, independently of the position of said actuating member.

Advantageously, said device comprises a cap which can be moved, in particular pivoting on the body, between a closed position of the mouthpiece and an open position of the mouthpiece, said cap cooperating with said actuating member such that, in the closed position, it blocks said actuating member against an axial movement in the body, and when it is returned from its open position to its closed position, it returns the actuating member to its rest position by reloading said spring.

Advantageously, said automatic valve release system comprises two levers, a push element and a lever spring, said push element being intended to come into contact with said reservoir, said push element being connected to said push member, with the interposition of said lever spring.

Advantageously, each lever is assembled via studs so as to pivot in a cam of said push member and cooperates with said push element in order to transmit the force exerted by said spring to said push element.

Advantageously, in the locked position, before inhalation, said levers bear on one side on a shoulder of said push element, and on the other side, said levers are in contact with locking fingers formed in said cover and which extend axially downwards from the bottom of said cover, said locking fingers preventing said levers from pivoting out of contact with said shoulder of said push element.

Advantageously, in the actuation position, after inhaling, said levers no longer cooperate with said locking fingers of said cover, so that they can then pivot in said push member out of contact with said shoulder of said push element, such that said reservoir can rise again towards its rest position under the effect of the return spring of said valve, with said levers passing through holes of said push element.

Advantageously, when the device is reset, when the user closes said cap, said actuating member and said push member return to their rest positions, compressing said spring, and said levers move axially with said push member until they come into contact with said locking fingers of said cover, which urge said studs to move radially outwards into said cams, which allows said levers to return around said locking fingers, said lever spring then returning said levers to bear on said shoulder of said push element.

Advantageously, said blocking element is mounted to pivot on the body about a pivot axis B, and said trigger element is mounted to pivot on the body about a pivot axis C, said axes B and C being parallel.

Advantageously, said actuating member that comprises an axial projection that cooperates with said blocking element, such that in the blocking position of said blocking element, said axial projection of said actuating member cooperates with an axial blocking extension of said blocking element, to thus prevent an axial movement of said actuating member, and in the actuation position of said blocking element, said axial projection of said actuating member cooperates with an axial recess of said blocking element thereby enabling said reservoir to move axially.

Advantageously, in the blocking position of said blocking element, said axial projection of said actuating member urges said blocking element towards its actuation position.

Advantageously, said blocking element comprises a locking projection that, in the locking position of the trigger element, cooperates with a locking shoulder of said trigger element so as to define a latch that prevents said blocking element from moving and/or deforming out of its blocking position.

Advantageously, in the locking position of the trigger element, said latch forms a first contact point between said blocking element and said trigger element, said blocking element comprising a bearing projection that, in the locking position of the trigger element, cooperates with a bearing surface of said trigger element so as to form, in the locking position of the trigger element, a second contact point between said blocking element and said trigger element, said second contact point being, in the locking position of the trigger element, at a distance from said axis C of the trigger element that is greater than the distance between said axis C and said first contact point.

Advantageously, said device comprises:
 a cover fixed, in particular screwed or snap-fitted, on said body, and
 a push member cooperating with said actuating member and mounted to slide axially in said cover, said spring being disposed between a bottom of said cover and said push member, wherein, before inhalation, said push member is out of contact with said reservoir, such that the force exerted on said push member by said spring is not transmitted to said reservoir, and during inhalation, said push member moves axially with said actuating member in order to come into contact with said reservoir and move said reservoir axially in said body in order to actuate said valve.

Advantageously, said device comprises an indicator to indicate to the user that the dispensing of fluid product has been made.

Advantageously, said indicator is a visual and/or audible indicator.

Advantageously, the device comprises an electronic meter.

Advantageously, before the first use of the device, said electronic meter is in standby mode, said electronic meter comprising a contactor, said actuating member, during its first movement towards its actuation position, contacting said contactor so as to put said electronic meter in normal operating mode.

Advantageously, said electronic meter comprises at least one accelerometer.

Advantageously, said inhalation-sensitive member comprises a deformable membrane that defines a deformable air chamber, said deformable membrane being fixed to said trigger element, said deformable membrane being deformed during inhaling, such that it moves said trigger element from its locking position towards its release position.

Advantageously, said mouthpiece comprises an opening that is connected to the inside of the body, said opening being closed at the start of inhaling by a check valve, such that the inhalation flow due to inhaling initially passes mainly to the trigger system.

Advantageously, said check valve is opened when said actuating member moves axially together with said reservoir.

Figure 2:
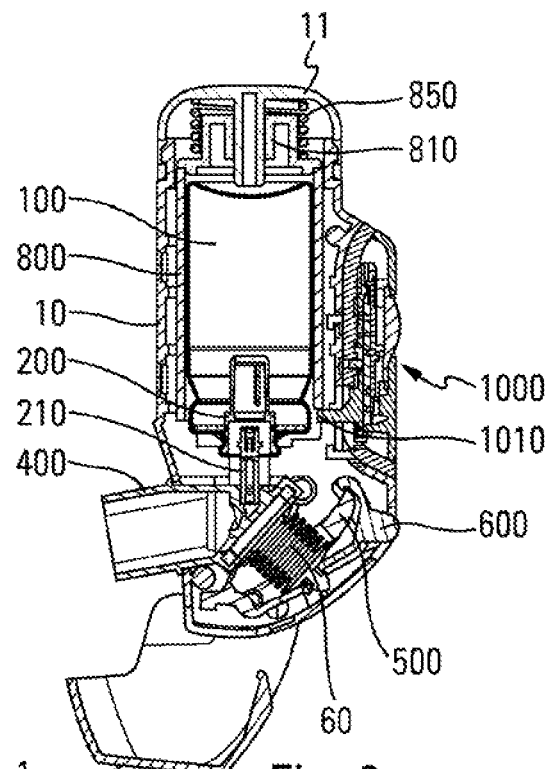
Figure 3:
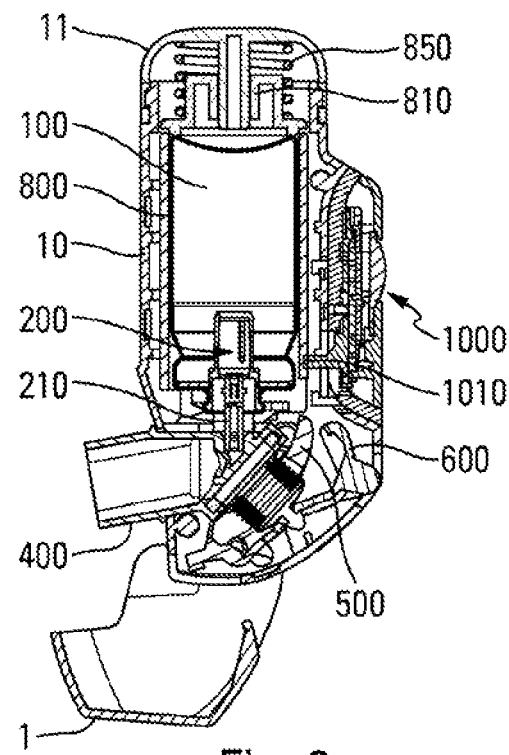
Figure 4:
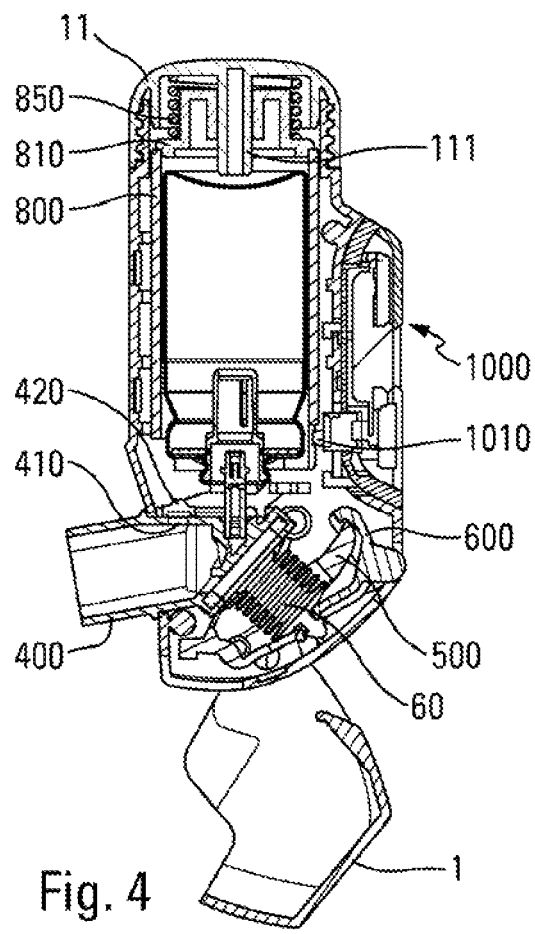
Figure 5:
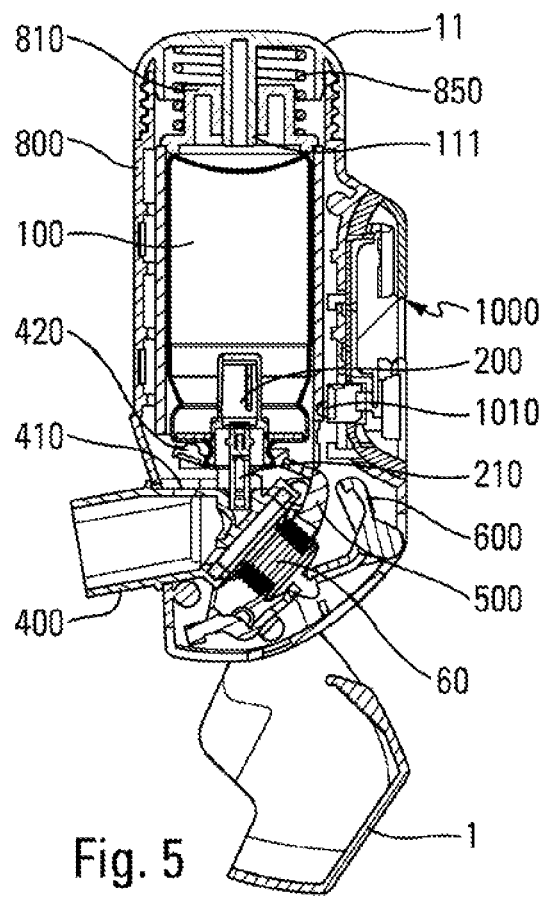
Figure 6:
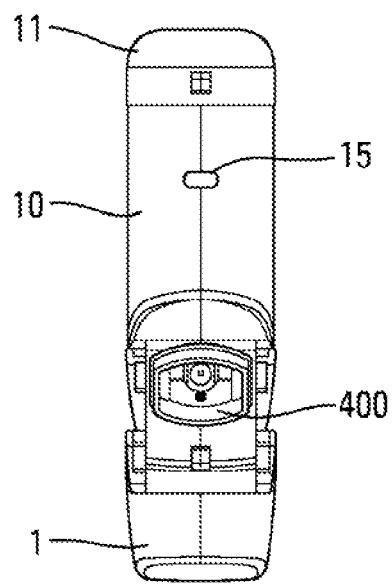
Figure 7:
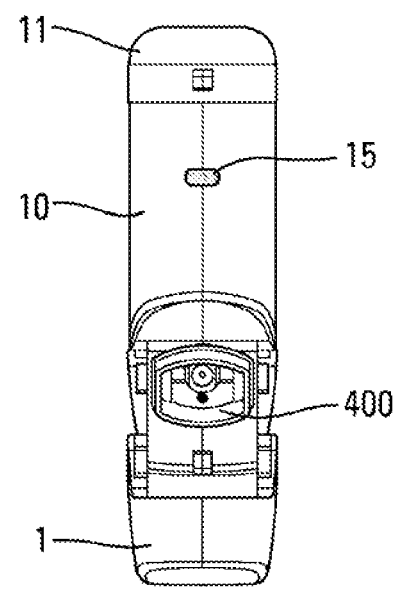
Figure 8:
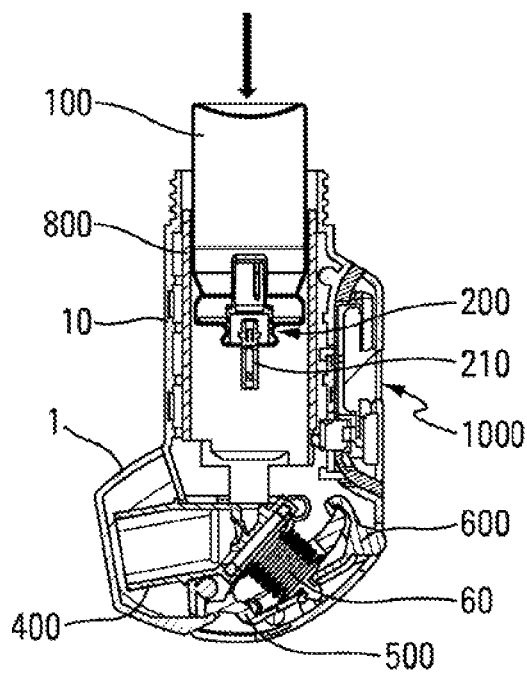
Figure 9:
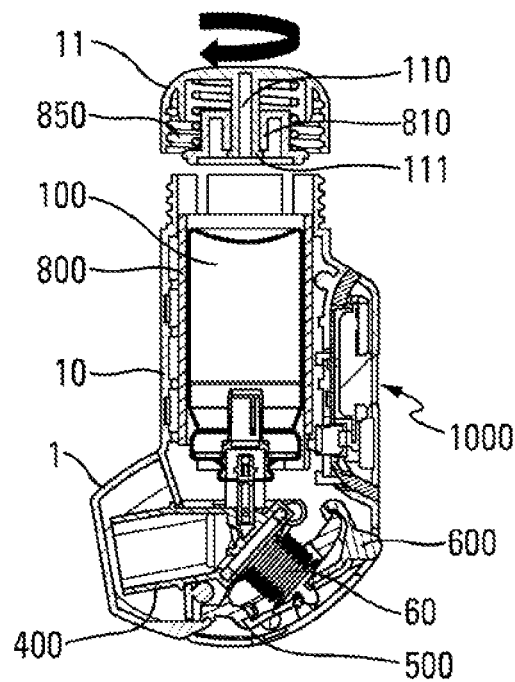
Figure 10:
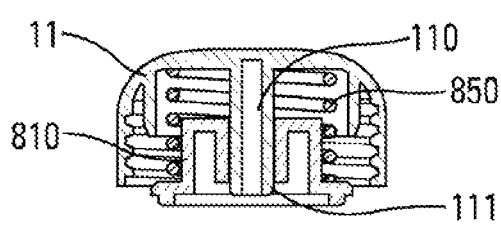
Figure 11:
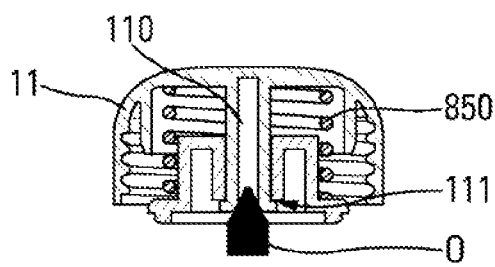
Figure 12:
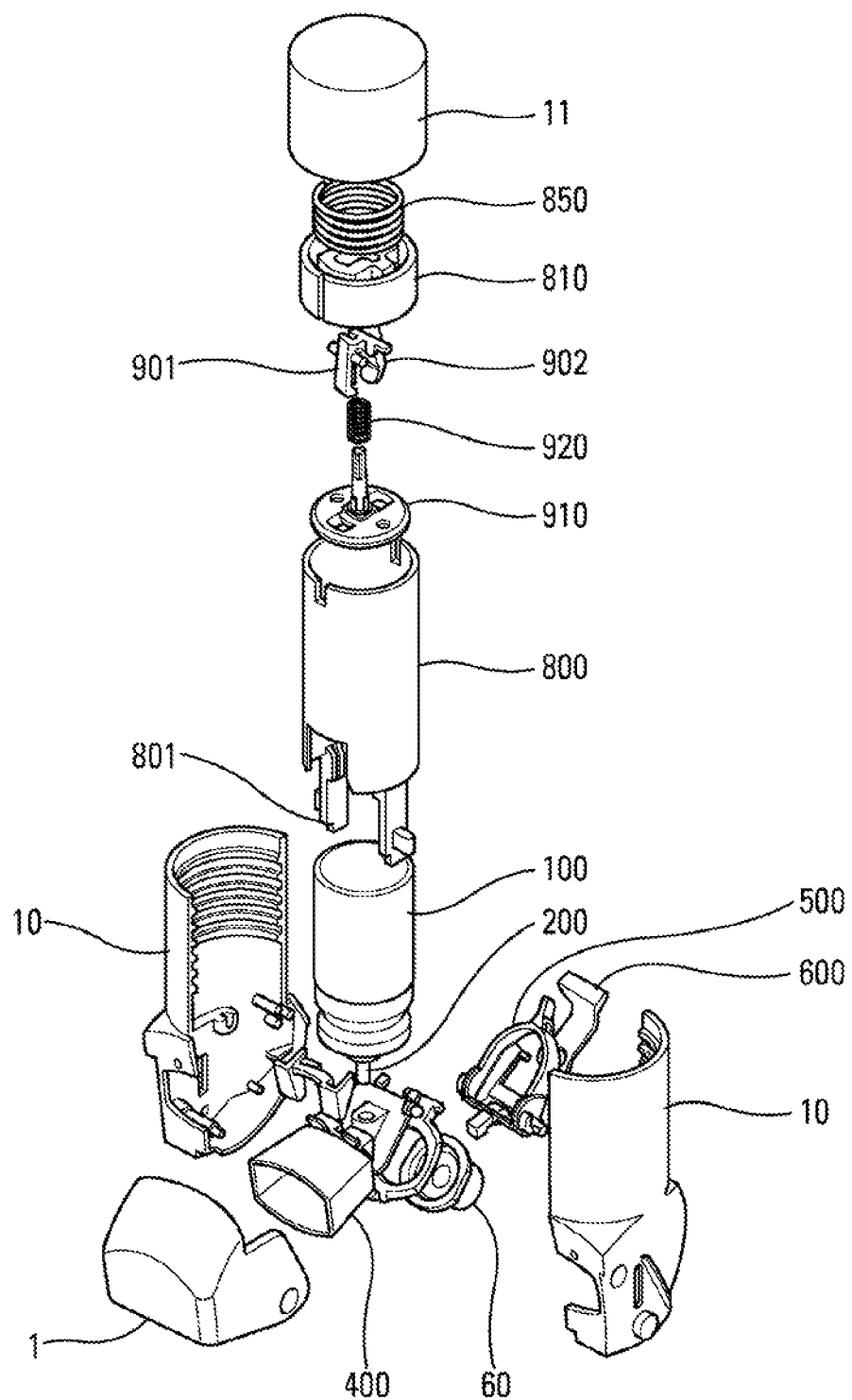
Figure 17:
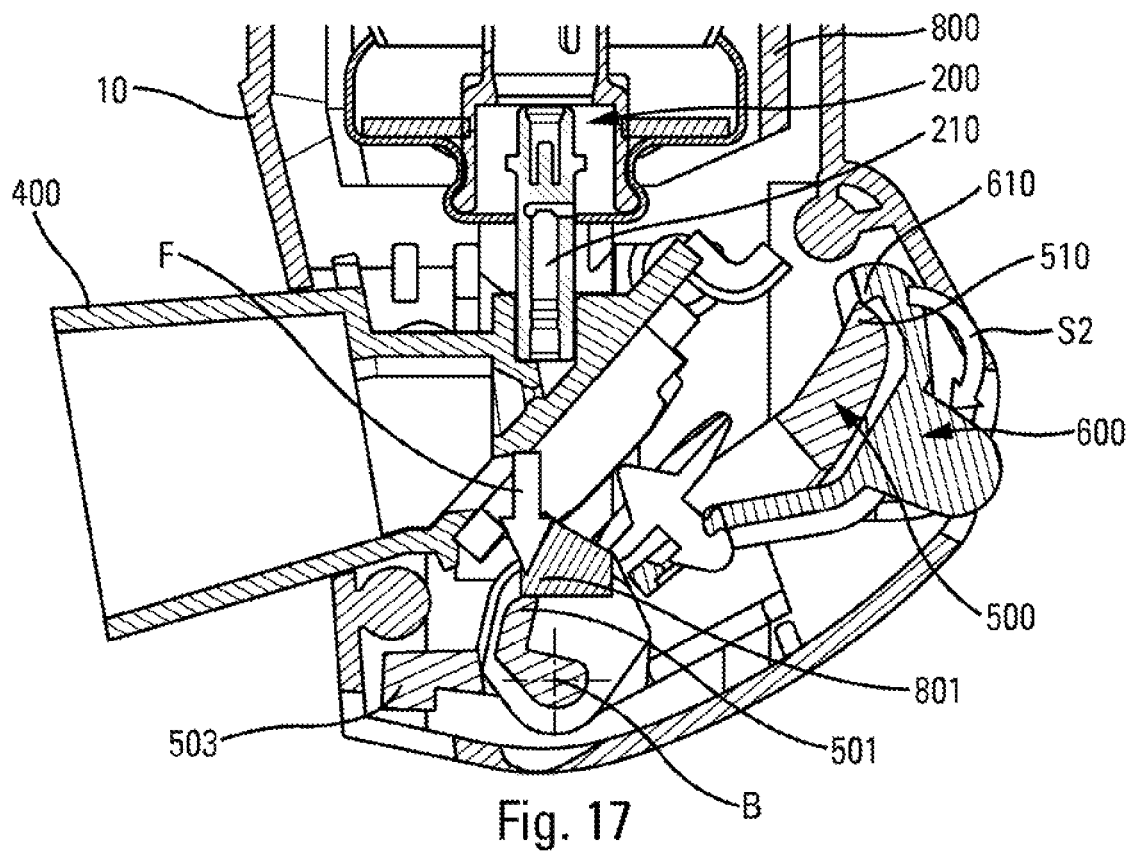
Figure 18:
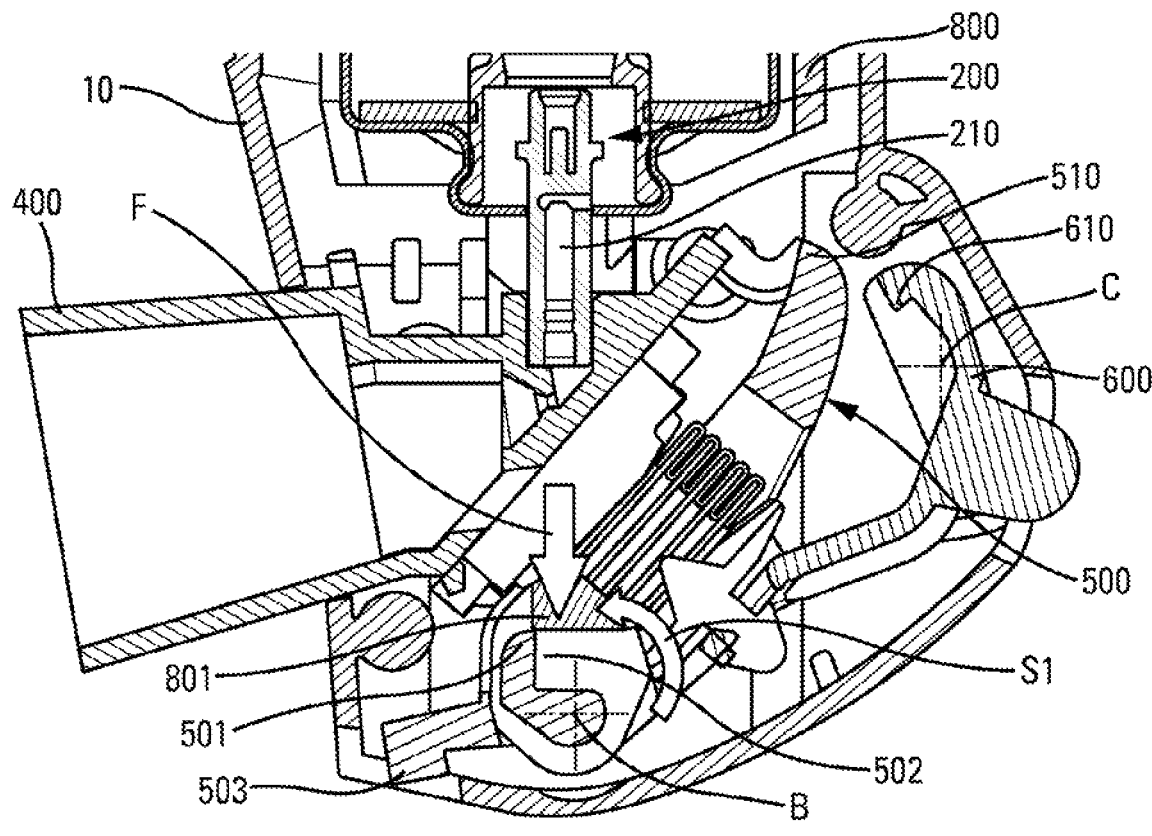

These and other characteristics and advantages will appear more clearly from the following detailed description made with reference to the accompanying drawings given by way of non-limiting examples, and wherein:

FIG. 1 is a diagrammatic section view transverse of a fluid product dispenser device in a first advantageous embodiment, in the rest position, FIG. 2 is a view similar to the view in FIG. 1, after cap has been opened and before inhalation, FIG. 3 is a view similar to the view in FIG. 2, shown after inhalation, FIG. 4 is a view similar to the view in FIG. 2, showing a variant embodiment, FIG. 5 is a view similar to the view in FIG. 4, shown after inhalation, FIG. 6 is a diagrammatic front view of the FIG. 1 device, shown before inhalation, FIG. 7 is a view similar to the view in FIG. 6, shown after inhalation, FIG. 8 is a diagrammatic section view of a variant embodiment of device in the FIG. 1, shown before assembly, FIG. 9 is a view similar to the view in FIG. 8, shown during assembly, FIG. 10 is a detailed diagrammatic view of a portion of the FIG. 9 device, shown before crimping, FIG. 11 is a view similar to the view in FIG. 10, shown after crimping, FIG. 12 is an exploded diagrammatic and perspective view of a fluid product dispenser device, in a second advantageous embodiment, FIGS. 13 to 15 are diagrammatic section views of the FIG. 12 device, respectively in its rest position, shown after opening the cap and before inhalation, and shown after inhalation, FIGS. 16 to 18 are enlarged diagrammatic views of the latch of the device in FIGS. 13 to 15, respectively shown before inhalation, at the beginning of inhalation and at the end of inhalation, FIGS. 19 to 22 are diagrammatic detailed views of the valve release system, during various stages of its actuation and resetting, FIG. 23 is a diagrammatic perspective, cross-sectional view of the push member, FIG. 24 is a diagrammatic perspective view of a valve release system lever, FIG. 25 is a diagrammatic perspective view of the push element of the valve release system, FIG. 26 is a diagrammatic perspective view of the actuating member, FIG. 27 is a diagrammatic perspective view of the cap, FIG. 28 is a diagrammatic perspective view of the trigger element, and FIG. 29 is a diagrammatic perspective view of the blocking element.

In the description, the terms "top", "bottom", "upwards", and "downwards" refer to the position of the device as shown in particular in FIGS. 1 to 9 and 13 to 15. The terms "axial" and "radial", unless specified otherwise, are relative to the vertical central axis of the valve. The terms "proximal" and "distal" are relative to the mouthpiece.

The invention applies more particularly to inhaler devices of the aerosol-valve type for oral dispensing, as described in greater detail below, but it could also apply to other types of inhaler device, e.g. of the nasal type.

The figures show various advantageous embodiments of the invention, but it is understood that one or more of the component parts described below could be made in some other way, while providing functions that are similar or identical.

With reference to the drawings, the device comprises a body 10 provided with a mouthpiece 400.

The body 10 may be made as a single piece or out of a plurality of parts that are assembled together. FIG. 12 shows an example in which the body 10 is formed of two half-shells, but other embodiments are possible. In the description below, the body is designated, in overall manner, by the numerical reference 10.

The mouthpiece 400 defines a dispensing orifice through which the user inhales while the device is being used. The mouthpiece 400 may be made integrally with the body 10. In the embodiments shown in the drawings, it is assembled on the bottom portion of the body 10.

A removable protective cap 1 is provided to cover said mouthpiece 400, in particular while it is being stored. This cap 1 is movable, preferably by being mounted to pivot on the body 10, between a closed position, shown in FIGS. 1, 8, 9, and 13, and an open position, shown in FIGS. 2 to 7, 14, and 15.

The body 10 contains a reservoir 100 that contains the product to be dispensed and a propellant gas, such as a gas of the hydrofluoroalkane (HFA) type, a metering valve 200 being mounted on said reservoir 100 for selectively dispensing the product. The metering valve 200 comprises a valve body and a valve member 210 that, during actuation, is axially movable relative to said valve body, and thus relative to said reservoir 100 between a rest position, and an actuation position. This metering valve 200 can be of any appropriate type. It is fixed to the reservoir 100 via an appropriate fixing element, preferably a crimped capsule, preferably with a neck gasket interposed therebetween.

Advantageously, during actuation, the valve member 210 is stationary relative to the body 10, and it is the reservoir 100 that is moved axially relative to the body 10 between a distal position, which is the rest position, and a proximal position, which is the actuation position.

The outlet orifice of the valve member 210 of said metering valve 200 is connected via a channel to said mouthpiece 400 through which the user inhales the product to be dispensed. In a known manner, said valve member 210 is received in a valve well 700 that at least partially defines said channel.

An actuating member 800 is advantageously assembled around the reservoir 100. This actuating member 800 comprises a hollow sleeve disposed in the body 10 around the reservoir 100. A push member 810 is mounted on the distal axial edge of said actuating member 800, said push member 810 being received in a cover element 11 fixed to the upper axial edge of said body 10. A spring 850 is disposed between a bottom of said cover element 11 and said push member 810. In the rest position, and until inhalation, the spring 850 is prestressed, and therefore exerts an axial force F on the push member 810 which transmits this force to the actuating member 800. The actuating member 800 is axially movable, in particular slidingly, relative to said body 10 between a rest position and an actuation position. A lower edge 802 of the actuating member 800 cooperates with the cap 1 such that, in the closed position of the cap 1, said actuating member 800 is blocked in the rest position, the lower edge 802 being in abutment against a portion 3 of said cap 1. Furthermore, said cap 1 comprises a cam 4 which cooperates with said lower edge 802 when the cap 1 is returned from its open position to its closed position, so as to return said actuating member 800 from its actuation position to its rest position. When the actuating member 800 returns towards its rest position, it also returns the push member 810, which causes the compression of the spring 850. The spring 850 is therefore reloaded after each actuation when the user closes the cap 1.

The device comprises a blocking element 500 that is movable and/or deformable between a blocking position in which said metering valve 200 cannot be actuated, and an actuation position in which said metering valve 200 can be actuated.

The blocking element 500 is advantageously mounted to pivot on the body 10 about an axis B (which can be seen better in FIGS. 16 to 18) between the blocking position and the actuation position.

Before inhalation, said blocking element 500 is in the blocking position, and it is the user inhaling through the mouthpiece 400 that moves and/or deforms said blocking element 500 towards its actuation position. In other words, so long as the user does not inhale, it is impossible to actuate the metering valve 200, and it is only when the user inhales that said metering valve 200 can be actuated, by moving the reservoir 100 axially in the body 10.

As described in greater detail below, the blocking element 500, in its blocking position, prevents the axial movement of the actuating member 800 in the body 10. During inhaling, this blocking element 500 is moved and/or deformed such that it no longer blocks the axial movement of the actuating member 800 in the body 10. Thus, after inhaling, such an axial movement of the actuating member 800 causes the axial movement of the reservoir 100 and therefore the actuation of the metering valve 200 and the dispensing of a dose of product, synchronously with this inhaling.

Thus, in the absence of inhaling, there is no risk of a dose of active product being lost by accidental or incomplete actuation in which the user does not inhale.

In the closed position of the cap 1, a blocking part 2 of the cap 1 cooperates with a projecting part 503 of the blocking member 500 in order to block the latter in the blocking position, as can be seen in particular in FIG. 1. This blocking is eliminated when the cap 1 is opened.

Opening the cap 1 therefore releases two blockages provided by the cap in the closed position: firstly, the blockage of the actuating member 800 in axial movement and secondly, the blockage the blocking member 500 in pivoting.

The device comprises a trigger system that is controlled by the user inhaling, and that is intended for moving and/or deforming said blocking element 500 from its blocking position towards its actuation position, when the user inhales through the mouthpiece 400.

This trigger system comprises an inhalation-sensitive member 60 that is deformable and/or movable under the effect of inhaling, this inhalation-sensitive member 60 being adapted, when it is deformed and/or moved, to make it possible to move and/or deform said blocking element 500 from its blocking position towards its actuation position.

As described in greater detail below, the inhalation-sensitive member may be made in the form of a deformable air chamber 60, e.g. a bellows or a deformable pouch.

The inhalation-controlled trigger system is thereby not located in the user's suction flow but is formed by a specific chamber, namely the air chamber 60. This differs from systems that operate by means of a flap that moves/deforms in the suction flow, systems in which, after triggering, the user sucks in the air that exists on each side of the flap. In this case, the system operates under reduced pressure and the user sucks in only the small volume of air that was inside the air chamber 60 before it deformed. The system according to the invention is thus much more stable and effective.

The blocking element 500 comprises at least one, preferably two, blocking extensions 501, each of which cooperates in the blocking position with an axial projection 801 of said actuating member 800. FIG. 29 is a perspective view of this blocking element 500.

When the blocking element 500 moves towards its actuation position, in particular by pivoting about the axis B, each blocking extension 501 moves out of contact with the respective axial projection 801. In particular, adjacent to each blocking extension 501, said blocking element 500 comprises an axial recess 502 which can be seen in FIG. 18, in which the respective axial projection 801 can slide axially, to thus enable an axial sliding of said actuating member 800 in said body 10, causing the reservoir 100 to move axially and the valve 200 to be actuated with the dispensing of a dose of fluid product.

The blocking element 500 is held in the blocking position by a trigger element 600. FIG. 28 is a perspective view of this trigger element 600. This trigger element 600 is advantageously mounted to pivot on the body 10 about an axis C (which can be seen in FIGS. 16 and 18), between a locking position in which it blocks said blocking element 500 in its blocking position, and a release position in which it no longer blocks said blocking element 500.

Advantageously, the axes B and C are parallel.

The blocking element 500 and the trigger element 600 together define a latch. In particular, said trigger element 600 comprises a locking shoulder 610 that, in the locking position, cooperates with a locking projection 510 of the blocking element 500, preventing said blocking element 500 from pivoting out of its blocking position. Thus, when said trigger element 600 is in the locking position, it prevents the blocking element 500 from moving towards its actuation position, which blocks the reservoir 100 from moving axially and the metering valve 200 from therefore being actuated.

The blocking system of the present invention therefore comprises two stages: a first stage formed by the latch between the blocking element 500 and the trigger element 600, and a second stage formed by the blocking between the blocking element 500 and the actuating member 800.

This blocking system makes it possible to unlock a large force (typically about 40N to 45N) by means of a small force generated by inhaling. The blocking element 500 stops the actuating member 800 from moving in translation when it is subjected to a force F (e.g. of 45N) by the spring 850 pressing on the actuating member 800 via the push member 810. This blocking element 500 interacts with the trigger element 600, and it is both blocked and released by said trigger element. The movement of said trigger element 600 is controlled by inhaling.

The shape of the blocking system enables very large amplification (unlocked force/unlocking force), typically of about 100.

The blocking element 500 and the trigger element 600 preferably have two contact points that are spaced apart:
  a first contact point, formed by the latch defined between the locking shoulder 610 and the projection 510, located advantageously close to the pivot axis C of the trigger element 600; —a second contact point spaced apart from the first contact point, formed by the cooperation between a lateral projection 520 of the blocking element 500 and a bearing surface 620 of the trigger element 600; advantageously, in the locking position, this second contact point is at a distance from the axis C of the trigger element 600 that is greater than the distance between said axis C and the first contact point;
    —advantageously, this second contact point is the first contact that is broken while actuating the device, when the user begins to inhale.

In the blocking position, after opening the cap 1 and before inhaling, the axial force F generated by the spring 550 on the actuating member 800 is applied by the axial projections 801 of the actuating member 800 to the blocking element 500 at the extensions 501, having the effect of urging said blocking element 500 in rotation in a first direction S1, which can be seen in FIG. 16, that reinforces the closed position of the latch and makes it stable.

The unlocking force generated by inhaling is applied to the trigger element 600 by the inhalation-sensitive member 60, preferably at a point 630 spaced apart from from the pivot axis C. This unlocking force seeks to pivot said trigger element 600 in the direction S2 opposite to the direction S1, as shown in FIG. 17.

The torque to which the blocking element 500 is subjected is controlled by the distance between the force axis along which the force F is applied to the blocking extensions 501 of the blocking element, and the pivot axis B of said blocking element 500. It is desirable for the distance d to be as small as possible, in order for the torque to be as small as possible. This distance d, shown in FIG. 16, is non-zero, and is less than 2 mm, advantageously less than 1 mm.

The torque to which the trigger element 600 is subjected is controlled by the distance d' between the force axis conveying the force F' to which the trigger element 600 is subjected by the blocking element 500, and the pivot axis C of said trigger element 600. Once again, it is desirable for the distance d' to be as small as possible, in order for the torque to be as small as possible. This distance d', shown in FIG. 16, is non-zero, and is less than 2 mm, advantageously less than 1 mm.

By means of this force system of the latch, the force necessary to cause the trigger element 600 to pivot is very small and may be generated by the inhalation-sensitive member 60 that makes it possible to transform the reduced pressure generated by inhaling into unlocking force.

Advantageously, as shown in the variant of FIGS. 4 and 5, the mouthpiece 400 comprises one or more opening(s) 410 that are connected to the inside of the body 10. This at least one opening 410 is closed at rest and at the start of inhaling by a check valve 420, such that the inhalation flow is initially mainly transmitted to the trigger system by inhaling, in this example, the deformable air chamber 60. This makes it possible to optimise this triggering by inhaling. When the blocking element 500 moves towards its actuation position under the effect of inhaling, and therefore the reservoir 100 moves axially relative to the body 10 so as to actuate the metering valve 200 in order to dispense a dose of fluid product, said actuating member 800, or alternatively said reservoir 100, moves said check valve 420 towards an open position. When said at least one opening 410 is thus opened, during actuation, air is drawn in, thereby making it possible to increase the inhalation flow. This optimises synchronization between the user inhaling and dispensing the dose, and also promotes good dispensing of the dose into the user's lungs.

Advantageously, the trigger element 600 may be accessible from the outside of the body 10. This makes it possible, if necessary, to move the trigger element 600 manually, so as to be able to actuate the metering valve 200 even without inhaling, e.g. if the person that needs to receive the dose of fluid is incapable of inhaling sufficiently. This is therefore a safety measure. This also makes it possible to prime the valve, if the latter is a conventional valve requiring such priming.

In the embodiments shown in the figures, the inhalation-sensitive member 60 is made in the form of a deformable air chamber. Advantageously, this air chamber comprises a deformable membrane that is connected firstly to said body 10 and secondly to said trigger element 600. Advantageously, as can be seen in the figures, the membrane is in the form of a bellows and forms a substantially sealed chamber. Other forms are possible, in particular a mere pouch or diaphragm. A stud may fix said membrane to an orifice or edge 630 of said trigger element 600.

During inhaling, the deformable membrane deforms and/or contracts under the effect of the suction generated by inhaling, causing the trigger element 600 to move from its locking position towards its release position. This makes it possible to open the latch defined between the blocking element 500 and the trigger element 600, and therefore to move said blocking element 500 from its blocking position towards its actuation position.

The valve 200 is therefore actuated only at the moment of inhaling, such that the dose of fluid product is expelled out of the dispensing orifice simultaneously with inhaling.

In the rest position, with the cap 1 closed, the push member 810 is not in contact with the reservoir 100, as can be seen in FIG. 1. Thus, in this position, the force of the spring 850 is applied by the push member 810 to the actuating member 800, which transmits it to the cap 1. Thus, during storage of the device, no stress is applied to the valve 200, which limits or even eliminates the risks of leakage and/or malfunction of said valve.

When the user wishes to use the device, the user opens the cap 1. In doing so, it prevents the actuating member 800 from being blocked axially by the cap 1 as well as the blocking element 500 from being blocked in terms of pivoting by the cap 1. In this position, the actuating member 800 is blocked and prevented from sliding axially in the body 10 by the blocking extensions 501 of the blocking element 500 that axially block the axial projections 801 of the actuating member 800. As can be seen in FIG. 2, in this armed position (cap open, before inhalation), the push member 810 is still not in contact with the reservoir 100. Thus, also in this position, the force of the spring 850 is applied by the push member 810 to the actuating member 800, which transmits it to the blocking element 500, which transmits it to the trigger element 600. Thus, before inhalation, no stress is applied to the valve 200, which limits or even eliminates the risks of leakage and/or malfunction of said valve.

When the user inhales through the mouthpiece 400, the deformable membrane of the inhalation-sensitive member 60 deforms, and this causes the trigger element 600 that is fixed to said deformable membrane to pivot. This movement of the trigger element 600 releases the latch formed between the locking shoulder 610 of the trigger element 600 and the projection 510 of the blocking element 500. Under the effect of the axial force F transmitted by the actuating member 800, the blocking element 500 pivots, enabling said actuating member 800 to slide axially. Consequently, the push member 810, integral with said actuating member 800, comes into contact with the reservoir 100, thus causing said reservoir 100 to move axially in the body 10 towards its dispensing position, and the valve 200 therefore to be actuated.

At the same time, in the variant of FIGS. 4 and 5, the actuating member 800 (or alternatively the reservoir 100) will open the valve 420.

At the end of inhalation, the device advantageously comprises signalling means for signalling to the user that he/she must close the cap 1. These signalling means may comprise a visual indicator, as shown in FIGS. 6 and 7. In this example, a window 15 is formed in the body 10, through which a coloured portion of the actuating member 800 is visible from the outside, forming indicating means. Thus, in the rest position or in the armed position, with the cap 1 open but before inhalation, the window 15 can indicate a light colour, for example green, whereas after inhalation, it is a dark colour, for example red, which can be displayed in the window 15. Naturally, any other similar embodiment is possible.

In a variant, it is possible to have several windows 15. The window(s) 15 may be positioned differently on the device, for example in the upper part of the body 10 or on the cover 11. The indication means which are displayed in the window 15 may, as a variant, comprise symbols, figures, letters or any other indication which is useful for alerting the user. These indicating means may be formed, for example formed by pad printing, directly on the actuating member 800, or may be formed on a part fixed thereto. The indicating means may be made on any other moving part during actuation, for example the push member 810, the blocking element 500, the trigger element 600, the inhalation-sensitive member 60.

In another variant, the signalling means may comprise an audible indicator, such as a loudspeaker, which emits a sound audible by the user to indicate to him/her that the cap 1 must be closed.

When the user closes the cap 1, the actuating member 800 is axially repelled by said cap 1 towards its rest position, such that said reservoir 100 can axially rise in the body 10 in the direction of its rest position under the effect of the return spring of the valve 200, and the valve member 210 of the metering valve simultaneously returns to its rest position, once again filling the valve chamber with a new dose of fluid product. The trigger element 600 is returned into its initial position, in particular by the springiness of the membrane. The blocking element 500 returns into its blocking position.

The device is thus ready for another use.

In an advantageous variant embodiment, shown in FIGS. 8 to 11, the final assembly of the device is simplified for the pharmaceutical laboratory which markets the device. In fact, in most existing devices, the reservoir filled with active principle is inserted into the body and then it is necessary to position several parts above the reservoir, which does not facilitate the production rates and the simplicity of assembly. To eliminate this drawback, the present invention advantageously provides for pre-assembling the subassembly formed by the push member 810, the spring 850 and the cover 11. This subassembly is prestressed during the assembly of these three parts, for example by coming with a hot tool O to thermally deform the lower axial edge 111 of a central axial sleeve 110 of the cover 11, around which the push member 810 and the spring 850 are assembled. Said lower axial edge 111 is thus deformed to produce a retention collar which retains the push member 810 and the spring 850 in the cover 11. This subassembly thus formed can then be assembled on the body 10 in a single assembly operation, for example by screwing or by snap-fitting. This then results in only two operations on the assembly line of the pharmaceutical laboratory: inserting the reservoir 100 in the body 10 (FIG. 8) and assembling said subassembly on said body 10 (FIG. 9). During this assembly, the actuating member 800 disposed in the body 10 will cooperate with the push member 810, so as to push it axially into the cover 11 and thus load the spring 850. In a screw-on version, this system can also make it possible to change the reservoir. Indeed, the device could be reusable and refillable for ecological reasons, in particular to avoid throwing away too many plastic components and/or too many electronic components.

In an advantageous embodiment, shown in FIGS. 12 to 15 and 19 to 22, the device comprises an automatic valve release system, which automatically returns the valve member 210 of the valve 200 towards its rest position after actuation of the valve, independently of the position of the cap 1 and of the position of the actuating member 800. Thus, in this variant, there is no risk of malfunction, such as an underdose of the next dose, even if the user delays closing the cap.

The valve release system comprises the following additional parts:
two levers 901, 902,
a push element 910,
a lever spring 920.

The push element 910 is intended to come into contact with the reservoir 100, and is connected to the push member 810, with the interposition of the lever spring 920. Advantageously, before inhalation, the push element 910 is very slightly offset axially from the reservoir 100, such that in this position, it transmits no stress to said reservoir 100 or to the valve 200. It is only when the user inhales, and releases the actuating member 800 from moving axially, that the push element 910 comes into contact with the reservoir 100.

Each lever 901, 902 is assembled via studs 905 so as to pivot in a cam 815 of the push member 810 and cooperates with said push element 910.

When the user inhales, the actuating member 800 and therefore the push member 810 move axially downwards under the effect of the spring 850. This force is transmitted by the levers 901, 902 to the push element 910, which transmits it to the reservoir 100, thus causing the axial movement of said reservoir 100 and the valve 200 to be actuated.

The aim of the valve release system is therefore to release the transmission of the force from the spring 850 to the reservoir 100 after inhalation, so as to enable said reservoir 100 to return towards its rest position independently of the actuating member 800. This makes it possible to load the next dose into the valve 200 immediately after inhalation, when the device is still in the appropriate position for this loading, without risk of incorrect dosing, for example in the case of forgetting to close the cap 1.

The valve release system operates as follows:

In the locked position, before inhalation, shown in FIG. 19, the levers 901 and 902 bear on a shoulder 911 of the push element 910. On the opposite side, the levers are in contact with locking fingers 115 formed in the cover 11 and which extend axially downwards from the bottom of said cover. These locking fingers 115 prevent the levers 901, 902 from pivoting out of contact with the shoulder 911 of the push element. In this position, the force of the spring 850 is therefore transmitted by the levers 901, 902 to the push element 910 and therefore to the reservoir 100.

When the actuating member 800 arrives in the actuation position, with the valve 200 which has been actuated to dispense a dose, the push member 810, the push element 910 and the levers 901, 902 have slid axially downwards relative to the cover 11, as can be seen in FIG. 20. In this position, the levers 901, 902 no longer cooperate with the locking fingers 115 of the cover 11. They can then pivot in the push member 810 until they are no longer in contact with the shoulder 911 of the push element. Advantageously, the release of the push element 910 occurs after the dose has been expelled by the valve, but before the end of the actuation stroke of the latter.

When the levers 901, 902 are no longer in contact with the shoulder 911 of the push element, each of them faces an opening 912 in said push element 910, such that the reservoir 100 can rise again towards its rest position under the effect of the return spring of the valve 200, with the levers 901, 902 passing through said holes 912, as can be seen in FIG. 21. During this return of the reservoir 100 towards its rest position, the push element 910 slides axially upwards together with the reservoir 100, with respect to the push member 810 and to the levers 901, 902. During this movement, the lever spring 920, the stiffness of which must be less than that of the spring of the valve 200, compresses.

When the device shown in FIG. 22 is reset, when the user closes the cap 1, the actuating member 800 and the push member 810 return to their rest positions, compressing the spring 850. During this movement, the levers 901, 902 undergo a force exerted by the lever spring 920, which urge them in rotation, as indicated by the arrow F1. As long as the levers 901, 902 are in the holes 912 of the push element 910, they cannot pivot and they move axially with the push member 810, as indicated by the arrow F2. When they come into contact with the locking fingers 115 of the cover 11, the studs 905 are forced to move radially outwards into the cams 815, as indicated by arrow F3, which allows the levers 901, 902 to return around said locking fingers 115 of the cover 11.

When the actuating member 800 and the push member 810 reach their rest positions, the levers 901, 902 have emerged from the holes 912 in the push element, and the lever spring 920 returns said levers to bear on the shoulder 911.

To ensure reliable operation of the device, the valve release system must be actuated only after a sufficient stroke to ensure that dose dispensing occurs. Because of the manufacturing tolerances of the parts, it may be advantageous to provide a buffer element between the push element 910 and the reservoir 100. This buffer element, which must slow down or offset the actuation of the valve release system, may be an elastic element, such as a spring or a compressible part, for example made of elastomer. Its resistance must be, on the one hand, greater than the force of the spring of the valve 200 in the actuation position of the valve 210, such that it is first of all the valve 200 which is actuated before the buffer element deforms, and, on the other hand, less than the force of the spring 850 in the actuation position of the actuating member 800, in order to guarantee that the buffer element will compress at the end of the actuating stroke. In a variant, it is also possible to use a buffer element formed by an actuator or by a variable-volume chamber, filled with air or a fluid, and provided with a leakage orifice.

In an advantageous embodiment, the device may comprise a dose meter 1000, shown in FIGS. 1 to 9, which may be mechanical or electronic, advantageously assembled in the body 10. Such a meter could also be associated with the embodiments in FIGS. 12 to 22. In particular, this meter 1000 can detect the movements of the actuating member 800 or of the reservoir 100. In a variant, the meter could be connected to a sensor, in particular a membrane sensor, that detects the dose of fluid product being dispensed, for example in the valve well. Such a meter could be actuated in other ways, for example by detecting the movement of the valve member 210 of the metering valve 200 relative to the valve body.

When the meter is electronic, it must be able to have enough electrical energy to operate throughout the storage period until its first use. The battery must then have a sufficient capacity, for example to communicate with the user (viewing the number of doses remaining) and/or with a third-party application, throughout its use and at least until the expiry date of the medicinal product. To avoid an excessively large battery, it is necessary to reduce the power consumption of the electronic board before first use. To do this, the electronics is advantageously put in a standby mode, which consumes little energy, until the moment of first use. To "wake up" the electronics, the user is asked to actuate the device by inhaling the first dose (if the device is provided with a valve without priming) or by priming (if the device is provided with a conventional valve). The first actuation causes the actuating member 800 to descend into the body 10. A portion of the actuating member 800 will then press on a contactor 1010, as shown in FIGS. 2 to 5, thereby closing a current loop. The device then detects this change in intensity, which will wake up the electronics and put the meter in a normal operating state.

In a variant, or additionally, the device may comprise an accelerometer.

This accelerometer can have several functions:
  it can be used to check that the device has indeed been shaken before use; indeed, most of the medicines stored in a pressurized reservoir are more or less soluble medicines and it is therefore necessary to mix them before taking a dose; if the electrical circuit senses via the accelerometer that the device has not been shaken, the user may be informed of this, for example by an application on its smartphone or on a screen of the device;
  some people take the device upside down when they wish to actuate it; when the device is upside down, i.e. with the reservoir disposed below the valve, the liquid cannot enter the dosing chamber of the valve, which results in a reduced or even zero dose when loading the dose; the accelerometer can detect whether the patient is taking the device upside down and indicate to them, preferably before taking the dose, for example by a beep sound and/or an indication on the screen and/or on the smartphone, that the device is not in the correct direction;
  another use of the accelerometer is to use it to save battery power; when the device is in a pouch or trouser pocket or placed on a table, the device is in standby mode; during this phase, the meter screen and a large portion of the onboard electronics are in standby mode, which greatly reduces power consumption; when the user grasps the device, the accelerometer detects movement and wakes up the electronics to put the meter in the normal operating condition; this option then makes it possible to reduce the capacity of the onboard battery and therefore to have a less negative impact on the environment.

The device may also comprise signal-transmitter means for communicating, in particular communicating remotely, information relating to the actuations of the device. In particular, the body and/or the cap and/or the meter may comprise a signal-transmitter module, for communicating remotely with any remote device. Appropriate power supply means are advantageously provided.

Advantageously, the electronic module may comprise a board comprising an electrical switch that sends a pulse. The module may also comprise a display unit and/or use a Bluetooth or Wi-fi connection for sending information to an accompanying peripheral. Appropriate sensors, such as flowrate and/or pressure sensors, may be provided for detecting various parameters of the inhalation flow.

The switch can be actuated by virtue of the movement of the actuating member and/or of the blocking element and/or of the trigger element and/or of the inhalation-sensitive member.

Associated with a dose meter that counts each dose that is actually dispensed, and with the inhalation-synchronized device of the invention, these signal-transmitter means make it possible for each dose that has been dispensed to be transmitted in completely reliable manner, for example to a doctor or to any other person wishing to monitor the use of the inhaler device by the user. The inhalation-synchronized device guarantees that the user inhales each time the user actuates the device, and the meter records each dose that is dispensed, as well as with various associated parameters, such as the timestamp for each dispensing. The doctor can thus know very accurately the conditions of use of the device by the user.

The present invention applies, in particular, to treating asthma attacks or chronic obstructive pulmonary disease (COPD), by using formulations of the following types: salbutamol, aclidinium, formoterol, tiotropium, budesonide, fluticasone, indacaterol, glycopyrronium, salmeterol, umeclidinium bromide, vilanterol, olodaterol, or striverdi, or any combination of these formulations.

The present invention has been described with reference to advantageous embodiments and variants, but naturally any modification could be applied thereto by a person skilled in the art, without going beyond the scope of the present invention, as defined by the accompanying claims.

The invention claimed is:

1. An inhalation-synchronized fluid product dispenser device comprising a body (10) provided with a mouthpiece (400), a product reservoir (100) containing a fluid product and a propellant gas being mounted to slide axially relative to said body (10), a metering valve (200), comprising a valve member (210) movable between a rest position and an actuation position, being assembled on said reservoir (100) for selectively dispensing the fluid product on each actuation, said device further comprising:
- a blocking element (500) that is movable and/or deformable between a blocking position in which said metering valve (200) cannot be actuated, and an actuation position in which said metering valve (200), can be actuated,
- a trigger element (600) that is movable and/or deformable between a locking position in which the trigger element blocks said blocking element (500) in the blocking position, and a release position wherein the trigger element does not block said blocking element (500),
- an inhalation-controlled trigger system comprising an inhalation-sensitive member (60) that is deformable and/or movable under the effect of inhaling, said inhalation-sensitive member (60) cooperating with said trigger element (600), such that when said inhalation-sensitive member (60) is deformed and/or moved, said inhalation-sensitive member moves and/or deforms said trigger element (600) towards the release position, thus making it possible to move and/or deform said blocking element (500) from the blocking position towards the actuation position, and
- an actuating member (800) that is movable between a rest position and an actuation position under the effect of a spring (850), said actuating member (800) cooperating with said blocking element (500) such that in blocking position said blocking element (500), said blocking element (500) prevents an axial movement of said actuating member (800), and in actuation position said blocking element (500), said blocking element (500) makes it possible to move said actuating member (800) axially,
said device comprising an automatic valve release system, which automatically returns said valve member (210) from said metering valve (200) towards the rest position after actuation of the metering valve, independently of the position of said actuating member (800).

2. The device according to claim 1, wherein said device comprises a cap (1) which can be moved between a closed position of the mouthpiece (400) and an open position of the mouthpiece (400), said cap (1) cooperating with the said actuating member (800) such that, in the closed position, said cap blocks said actuating member (800) against an axial movement in the body (10), and when said cap is returned from the open position to the closed position, said cap returns the actuating member (800) to the rest position by reloading said spring (850).

3. The device according to claim 2, wherein said automatic valve release system comprises two levers (901, 902), a push element (910) and a lever spring (920), said push element (910) being intended to come into contact with said reservoir (100), said push element (910) being connected to a push member (810), with the interposition of said lever spring (920).

4. The device according to claim 3, wherein each lever (901, 902) is assembled via studs (905) so as to pivot in a cam (815) of said push member (810) and cooperates with said push element (910) so as to transmit the force (F) exerted by said spring (850) to said push element (910).

5. The device according to claim 4, wherein in the locked position, before inhalation, said levers (901, 902) bear on one side on a shoulder (911) of said push element (910), and on the other side said levers (901, 902) are in contact with locking fingers (115) formed in a cover (11) and which extend axially downwards from the bottom of said cover (11), said locking fingers (115) preventing said levers (901, 902) from pivoting out of contact with said shoulder (911) of said push element (910).

6. The device according to claim 5, wherein, in the actuation position, after inhalation said levers (901, 902) no longer cooperate with said locking fingers (115) of said cover (11), such that they can then pivot in said push member (810) out of contact with said shoulder (911) of said push element (910), such that said reservoir (100) can rise towards its rest position under the effect of the return spring of said valve (200), with said levers (901, 902) passing through holes (912) in said push element (910).

7. The device according to claim 6, wherein when the device is reset, when the user closes said cap (1), said actuating member (800) and said push member (810) return to their rest positions, compressing said spring (850), and said levers (901, 902) move axially with said push member (810) until they come into contact with said locking fingers (115) of said cap (11), which urge said studs (905) to move radially outwards in said cams (815), which allows said levers (901, 902) to return around said locking fingers (115), said lever spring (920) then returning said levers (901, 902) to bear on said shoulder (911) of said push member (910).

8. The device according to claim 1, wherein said blocking element (500) is mounted to pivot on the body (10) about a pivot axis (B), and said trigger element (600) is mounted to pivot on the body (10) about a pivot axis (C), said axes (B) and (C) being parallel.

9. The device according to claim 1, wherein said actuating member (800) comprises an axial projection (801) cooperating with said blocking element (500), such that in the blocking position of said blocking element (500), said axial projection (801) of said actuating member (800) cooperates with an axial blocking extension (501) of said blocking element (500) to thus prevent an axial movement of said actuating member (800), and in the actuation position of said blocking element (500), said axial projection (801) of said actuating member (800) cooperates with an axial recess (502) of said blocking element (500) thereby enabling said reservoir (800) to move axially.

10. The device according to claim 9, wherein, in the blocking position of said blocking element (500), said axial projection (801) of said actuating member (800) urges said blocking element (500) towards the actuation position.

11. The device according to claim 1, wherein said blocking element (500) comprises a locking projection (510) that, in the locking position of the trigger element (600), cooperates with a locking shoulder (610) of said trigger element (600) so as to define a latch that prevents said blocking element (500) from moving and/or deforming out of the blocking position.

12. The device according to claim 11, wherein in the locking position of the trigger element (600), said latch forms a first contact point between said blocking element (500) and said trigger element (600), said blocking element (500) comprising a bearing projection (520) that, in the locking position of the trigger element (600), cooperates with a bearing surface (620) of said trigger element (600) so as to form, in the locking position of the trigger element (600), a second contact point between said blocking element (500) and said trigger element (600), said second contact point being, in the locking position of the trigger element (600), at a distance from said axis (C) of the trigger element (600) that is greater than the distance between said axis (C) and said first contact point.

13. The device according to claim 1, wherein said device comprises:
a cover (11) which is fixed to said body (10), and—a push member (810) cooperating with said actuating member (800) and mounted to slide axially in said cover (11), said spring (850) being disposed between a bottom of said cover (11) and said push member (810), wherein, before inhalation, said push member (810) is out of contact with said reservoir (100), such that the force exerted on said push member (810) by said spring (850) is not transmitted to said reservoir (100), and during inhalation, said push member (810) moves axially with said actuating member (800) so as to come into contact with said reservoir (100) and move said reservoir (100) axially in said body (10) so as to actuate said valve (200).

14. The device according to claim 1, comprising an indicator (15) for indicating to the user that the dispensing of fluid product has been made.

15. The device according to claim 14, wherein said indicator is a visual indicator and/or audible indicator.

16. The device according to claim 1, comprising an electronic meter (1000).

17. The device according to claim 16, wherein, before the first use of the device, said electronic meter (1000) is in standby mode, said electronic counter comprising a contactor (1010), said actuating member (800), during a first movement of said actuating member towards the actuation position, contacting said contactor (1010) so as to place said electronic meter (1000) in normal operating mode.

18. The device according to claim 16, wherein said electronic meter (1000) comprises at least one accelerometer.

19. The device according to claim 1, wherein said inhalation-sensitive member (60) comprises a deformable membrane that defines a deformable air chamber, said deformable membrane being fixed to said trigger element (600), said deformable membrane being deformed during inhaling, such that said deformable membrane moves said trigger element (600) from the locking position towards the release position.

20. The device according to claim 1, wherein said mouthpiece (400) comprises an opening (410) that is connected to an inside of the body (10), said opening (410) being closed at the start of inhaling by a check valve (420), such that the inhalation flow due to inhaling initially passes mainly to the inhalation-controlled trigger system.

21. The device according to claim 20, wherein said check valve (420) is opened when said actuating member (800) moves axially together with said reservoir (100).

* * * * *